United States Patent
Rath et al.

(10) Patent No.: US 9,622,482 B2
(45) Date of Patent: Apr. 18, 2017

(54) METHODS FOR INCREASING OIL PALM YIELD

(71) Applicant: Valent BioSciences Corporation, Libertyville, IL (US)

(72) Inventors: Andrew Rath, Underwood (AU); Peter D. Petracek, Grayslake, IL (US); Gregory D. Venburg, Deerfield, IL (US); Warren E. Shafer, Libertyville, IL (US)

(73) Assignee: Valent BioSciences Corporation, Libertyville, IL (US)

(*) Notice: Subject to any disclaimer, the term of this patent is extended or adjusted under 35 U.S.C. 154(b) by 0 days.

(21) Appl. No.: 14/708,666

(22) Filed: May 11, 2015

(65) Prior Publication Data

US 2015/0320048 A1    Nov. 12, 2015

Related U.S. Application Data

(60) Provisional application No. 61/991,787, filed on May 12, 2014.

(51) Int. Cl.
| | | |
|---|---|---|
| *A01N 59/16* | (2006.01) | |
| *A01N 27/00* | (2006.01) | |
| *A01N 37/36* | (2006.01) | |
| *A01N 37/44* | (2006.01) | |
| *A01N 37/10* | (2006.01) | |
| *A01N 63/02* | (2006.01) | |
| *A01N 43/90* | (2006.01) | |

(52) U.S. Cl.
CPC ............. *A01N 59/16* (2013.01); *A01N 27/00* (2013.01); *A01N 37/10* (2013.01); *A01N 37/36* (2013.01); *A01N 37/44* (2013.01); *A01N 43/90* (2013.01); *A01N 63/02* (2013.01)

(58) Field of Classification Search
CPC ........ A01N 59/16; A01N 27/00; A01N 37/36; A01N 37/44; A01N 37/10; A01N 63/02; A01N 43/90
See application file for complete search history.

(56) References Cited

U.S. PATENT DOCUMENTS

| | | |
|---|---|---|
| 5,834,403 A | 11/1998 | Callan |
| 2007/0265166 A1 | 11/2007 | Bardella et al. |
| 2008/0039322 A1 | 2/2008 | Wang et al. |
| 2011/0318470 A1 | 12/2011 | Grossmann et al. |
| 2012/0322662 A1 | 12/2012 | Yoo et al. |
| 2013/0298290 A1 | 11/2013 | Haas et al. |

FOREIGN PATENT DOCUMENTS

WO    WO 2011/161132    12/2011

OTHER PUBLICATIONS

Tarmizi, A.H., Studies Towards Understanding Proline Accumulation in Oil Palm (*Elaeis guineensis* Jacq) Polyembryogenic Cultures Abstract, 2000, Journal of Oil Research Malasia, vol. 12, No. 1, Abstract.*
International Search Report and Written Opinion issued Jul. 28, 2015 in corresponding PCT Application No. PCT/US2015/030139.
Nualwijit et al. "Ripening delay and reduction of free fatty acids of oil palm fruit in response to 1-methylcyclopropene", Acta Hortic. (ISHS) 1011:343-349, (2013).
UNEP Global Environmental Alert Service (GEAS) "Oil palm plantations: threats and opportunities for tropical ecosystems", Dec. 2011.
Chan et al., "Effects of growth regulators on fruit abscission in oil palm, *Elaeis guineensis*" Ann. appl. Biol. (1972), 71, pp. 243-249.
Tranbarger et al., "Regulatory mechanisms underlying oil palm fruit mesocarp maturation, ripening, and functional specialization in lipid and carotenoid metabolism", Plant Physiology, Jun. 2011, vol. 156, pp. 564-584.

* cited by examiner

*Primary Examiner* — John Pak
*Assistant Examiner* — Andriae M Holt
(74) *Attorney, Agent, or Firm* — Wood, Phillips, Katz, Clark & Mortimer

(57) ABSTRACT

The present invention is directed to methods of using ethylene antagonists on oil palm before harvest of the oil palm fruit to increase oil production, wherein the ethylene antagonist is not 1-methylcyclopropene (1-MCP) or aminoethoxyvinylglycine (AVG).

4 Claims, No Drawings

METHODS FOR INCREASING OIL PALM YIELD

FIELD OF THE INVENTION

The present invention is directed to methods of using ethylene antagonists on oil palm prior to harvest of the oil palm fruit to increase oil production, wherein the ethylene antagonist is not 1-methylcyclopropene (1-MCP) or aminoethyoxyvinylglycine (AVG).

BACKGROUND OF THE INVENTION

Oil palms (Elaeis guineensis, Elaeis oleifera, or a cross thereof) are palms that are grown to produce oil. Oil palms grow up to 20 meters tall. Their fruit is reddish in color and about the size of a plum. The fruits grow in large bunches which grow around the palm. The time from pollination of the flowers to maturation of the fruit is about five to six months. Oil palms produce bunches year-round and the fruits are harvested as they reach maturity.

The oil palm's fruit consists of a fleshy outer layer that surrounds a palm kernel. Oil is extracted from the pulp of the fleshy outer layer and from the kernel. Oil palm is an important crop for vegetable oil production and is grown on about 15 million hectares worldwide (UNEP Global Environmental Alert Service, December 2011). The demand for palm oil is expected to double by 2020. To meet the increasing demand for palm oil and improve efficiency, agronomic methods such as tree spacing, increased planting, fertilization, and irrigation as well as genetic improvement have been developed to optimize oil production (Corley, R. H. V. and P. B. Tinker, 2003, The Oil Palm, $4^{th}$ edition, New York, John Wiley and Sons, 590 pp). There is still a need, however, for methods to increase production of currently planted oil palms. There is also still a need to increase oil production in order to maximize the oil production of the plants produced through genetic improvement. Further, there is a need to increase oil production of the palms managed by spacing, increased planting, fertilization, and irrigation.

Ethylene is a two carbon gaseous hydrocarbon molecule that acts as a regulator of plant growth and development. Ethylene plays important roles in many physiological processes through the lifecycle of plants including the promotion of germination, reduction of early plant growth, increase in male flower number, abscission of flowers and fruit, and promotion of ripening (Abeles, F. A., et. al., 1992, P. W. Morgan and M. E. Saltveit, Ethylene in Plant Biology, 2nd edition, 414 p., Academic Press, New York, 1992).

The effect of ethylene on the oil content of oil palm fruit is not well understood, however, the available literature suggests that application of ethylene increases oil content. For example, Chan, et al. (1972, Ann. Appl. Biol. 71:243-249) showed that preharvest application of the ethylene-releasing agent ethephon (2-chloroethyl phosphonic acid) to attached bunches of oil palm fruit increased oil content by 7%. Tranbarger, et al. (2011, Plant Physiol. 156:564-584) found concomitant increase in preharvest oil content and the ethylene level generated endogenously in the oil palm fruit. These reports suggest a relationship between increased ethylene levels and increased palm oil content.

Despite showing promise as a way to increase oil content, ethylene has numerous negative effects on plants which are well known in plant physiology. For example, ethylene promotes abscission of fruits and flowers which would decrease yield and yield potential. In fruit trees and bulbs, ethylene can cause the physiological disease gummosis. Gummosis is a generalized disorder of trees in which polysaccharide gum is overproduced, exuded, and deposited on the bark. Gummosis affects water relations, promotes disease, is attractive to wood-boring insects, causes shoot death, and leads to early tree decline. Based on these effects, application (particularly repeated application) of ethylene may not provide an overall benefit in oil palm.

In addition, few studies have examined the effect of ethylene antagonists on oil palm and of those studies, ethylene antagonists were applied after harvest. For example, Henderson and Osborne (1994) showed that a postharvest application of the ethylene biosynthesis inhibitor aminooxyacetic acid (AOA) delayed or suppressed abscission of oil palm fruit in detached bunches (J. Exper. Bot. 45:943-951). Based on this study and others, it is unclear whether ethylene antagonists will be beneficial as a pre-harvest treatment.

Accordingly, there is a need for practical methods to increase the amount of oil that oil palm trees produce. These methods should produce more oil while not harming the oil palm and should be easy to apply to the fruit or oil palm.

SUMMARY OF THE INVENTION

In one aspect, the invention is directed to methods of increasing the content of oil in oil palm fruits by application of an ethylene antagonist to the oil palm fruit before the oil palm fruit is harvested.

DETAILED DESCRIPTION OF THE INVENTION

Ethylene antagonists include ethylene biosynthesis inhibitors and ethylene action inhibitors. Ethylene biosynthesis inhibitors include AOA, rhizobitoxin, and cobalt ion. Ethylene action inhibitors include biologically active cyclopropenes such as 3-cyclopropyl-1-enyl-propanoic acid, 2,5-norbornadiene, silverthiosulfate (STS), and silver nitrate. As used herein, "ethylene antagonists," "ethylene action inhibitors," and "biologically active cyclopropenes" do not include 1-MCP. As used herein, "ethylene antagonists" and "ethylene action inhibitors" do not include AVG.

In one embodiment, the invention is directed to methods for increasing oil content of oil palm fruit comprising applying an ethylene antagonist to oil palm fruit before the oil palm fruit is harvested. In a preferred embodiment, the ethylene antagonist is an ethylene biosynthesis inhibitor selected from the group consisting of AOA and rhizobitoxin or an ethylene antagonist is an ethylene action inhibitor selected from the group consisting of cyclopropenes, 2,5-norbornadiene, silverthiosulfate, and silver nitrate. In a more preferred embodiment, the ethylene antagonist is the ethylene action inhibitor silverthiosulfate.

In another preferred embodiment, the cyclopropenes are selected from the group consisting of cyclopropenes with higher order substituents than methyl, such as a saturated or unsaturated, linear or branched chain, substituted or unsubstituted alkyl, alkenyl, or alkynyl (e. g. 1-ethylcyclopropene, 1-propylcyclopropene, 1-butylcyclopropene, 1-pentylcyclopropene, 1-hexylcyclopropene, 1-heptylcyclopropene, 1-octylcyclopropene), or a substituted alkyl, alkenyl, or alkynyl containing oxygen, nitrogen, sulfur, silicon or halogen (e.g. 1-(3-phenylpropyl)cyclopropene, 1-(4-phenyloxybutyl)cyclopropene, N,N-dipropyl (1-cyclopropenylmethyl) amine and salts or derivatives thereof, 1-cyclopropene-1-propanoic acid or salts or derivatives thereof (Plant Growth Reg. 2003, 40, 223-228; Plant Growth Reg. 2004, 42, 29-38; Plant Growth Reg. 2005, 47, 29-38; Plant Growth Reg. 2008, 55, 101-113; Postharvest Biol. Tech. 2009, 51, 43-38; Plant Growth Reg. 2011, 65, 327-334).

In another preferred embodiment, the cyclopropenes are generated in situ from cyclopropene precursors. In one embodiment, the cyclopropene precursors are selected from analogs of methyl-2(5H)-furanone, analogs of methyl-2 (3H)-furanone, analogs of 1-methyl-3-oxabicyclo[3.1.0] hexa-2,4-dione, and analogs of 3,4-dioxa-1-methyl-bicyclo [4.1.0]hepta-2,5-dione, and the cyclopropenes are generated via photolysis of these precursors. In a preferred embodiment, the cyclopropene precursors are selected from 1-substituted-1-(methanesulfonyloxy)-2-silyl-cyclopropanes such as trans-1-ethyl-1-(methanesulfonyloxy)-2-trimethlsilyl-cyclopropane, trans-1-propyl-1-(methanesulfonyloxy)-2-trimethlsilyl-cyclopropane, trans-1-butyl-1-(methanesulfonyloxy)-2-trimethylsilyl-cyclopropane, trans-1-pentyl-1-(methanesulfonyloxy)-2-trimethylsilyl-cyclopropane, trans-1-hexyl-1-(methanesulfonyloxy)-2-trimethylsilyl-cyclopropane, trans-1-(3-phenylpropyl)-1-(methanesulfonyloxy)-2-trimethylsilyl-cyclopropane, trans-1-(4-phenyloxybutyl)-1-(methanesulfonyloxy)-2-trimethylsilyl-cyclopropane, trans-1-(3-methoxybutyl)-1-(methanesulfonyloxy)-2-trimethlsilyl-cyclopropane, and the cyclopropenes are generated by treating the precursors with a fluoride salt such as tetraalkylammonium fluoride (see U.S. Patent Application Publication No. 2012/0322662).

The timing of application of an ethylene antagonist to the fruit is after the palm is sexually mature, but prior to harvest. This timing range does not include when the oil palm is a seedling. Preferably, the timing range is from initial flowering to prior to harvest. More preferably, the timing range is from just prior to initial fruit drop through early fruit drop from the most mature bunch or bunches on the oil palm. This timing corresponds to about 3 to 4 weeks before harvest to the day of harvest.

The ethylene antagonist may be applied in one treatment or during multiple treatments. In a preferred embodiment, the ethylene antagonist is applied 2 to 8 times. In a more preferred embodiment, the ethylene antagonist is applied 2 to 6 times. In a most preferred embodiment, the ethylene antagonist is applied 3 to 5 times to the fruits before they are harvested. If the ethylene antagonist is applied multiple times, then the preferred interval of application is about every 7 to 21 days. The most preferred interval of application is about every 10 to 14 days.

Preferably, the concentration of ethylene antagonist in an ethylene antagonist formulation that is applied to the plant is from about 0.2 to about 33,000 ppm. The more preferred concentration is from about 2 to about 6,600 ppm. The most preferred concentration is from about 240 to about 6,600 ppm.

Preferably, the volume of the application is from about 20 to about 2000 ml of a formulation containing an ethylene antagonist per palm plant. The most preferred volume of application is from about 100 to about 600 ml of a formulation containing an ethylene antagonist per palm plant. Amounts within the preferred volume ranges provide adequate coverage of the fruit.

Preferably, the volume of the formulation applied to each bunch on the plant is from about 1 to about 300 ml of the formulation containing an ethylene antagonist per bunch. In a more preferred embodiment, the volume of the formulation applied to each bunch on the plant is from about 50 to about 150 ml of the formulation containing an ethylene antagonist per bunch.

Preferably, the dose is from about 0.02 mg to about 20 g of ethylene antagonist per palm per application. The more preferred dose is from about 0.2 mg to about 2 g of ethylene antagonist per palm per application. The most preferred ethylene antagonist dose is from about 2 mg to about 0.2 g of ethylene antagonist per palm per application.

If there are approximately 135 oil palms per hectare of land, a preferred dose is from about 2 mg/ha to about 100 g/ha of an ethylene antagonist per application. The more preferred dose is from about 10 mg/ha to about 75 g/ha of an ethylene antagonist per application. The most preferred dose is from about 10 mg/ha to about 10 g/ha of an ethylene antagonist per application. If the density of oil palms is greater than or less than 135 oil palms per hectare of land, then the preferred dose may be proportionally increased or decreased.

Adjuvants such as surfactants, humectants, stickers, spreaders, urea, oils, and salts may be incorporated in a formulation containing the ethylene antagonist to improve performance.

An ethylene antagonist may be used in combination with one or more other plant growth regulators such as auxins, cytokinins, gibberellins, gibberellin antagonists, salicylic acid, methyl salicylate, methyl jasmonate, S-abscisic acid (ABA) or ABA analogs. One preferred ABA analog is 3'-methyl-ABA.

Auxins include but are not limited to 1-naphthyleneacetic acid (NAA), indolebutyric acid (IBA), or 2,4-dichlorophenoxyacetic acid (2,4-D). One preferred auxin is NAA.

Cytokinins include but are not limited to 6-benzyladenine (6BA), forchlorfenuron (CPPU), thidiazuron (TDZ), or kinetin. One preferred cytokinin is 6BA.

Gibberellins include but are not limited to GA3 (gibberellic acid), GA4, or GA7, or a combination of GA4 and GA7 (GA4/GA7).

Gibberellin antagonists include but are not limited to daminozide, mepiquat chloride, paclobutrazol, prohexadione calcium, trinexapac-ethyl, or uniconazole-P.

An ethylene antagonist or a composition comprising an ethylene antagonist, may be foliar applied to aerial parts of the oil palm including bunches and fronds by methods such as backpack sprayers, mist blowers, tractor or ATV-mounted sprayers or aerial application. The most preferred foliar application is targeted to the oldest bunches of fruits on the palm. An ethylene antagonist, or a composition comprising an ethylene antagonist, may also be applied to the ground by fumigation, drip irrigation or fertigation with nutrients or applied by trunk or bunch injection.

As used herein, an "ethylene antagonist" refers to a compound that reduces or eliminates ethylene activity by inhibiting ethylene biosynthesis or by preventing ethylene from binding to active receptor sites in an oil palm by blocking or modifying the ethylene receptor site.

As used herein, an "ethylene biosynthesis inhibitor" is a compound that inhibits ethylene biosynthesis and thus reduces ethylene levels.

As used herein, an "ethylene action inhibitor" is a compound that inhibits ethylene activity by blocking or modifying the ethylene receptor sites in oil palm and thereby preventing ethylene from binding to the ethylene receptor sites.

As used herein, "yield" refers to the amount of oil that is produced from the oil palm.

As used herein, "prior to harvest," "before harvest," and "preharvest" all refer to a time before the bunches and their fruits are harvested from the oil palm.

Throughout the application, the singular forms "a," "an," and "the" include plural reference unless the context clearly dictates otherwise.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

These representative embodiments are in no way limiting and are described solely to illustrate some aspects of the invention.

EXAMPLE

Example 1

A study was conducted in a plantation in Costa Rica to compare the effects of single bunch-directed applications of: (1) untreated control (water sprayed); (2) AVG at 500 ppm active ingredient (a.i.); (3) 240 ppm a.i. of STS; (4) 720 ppm a.i. of STS; (5) 2,200 ppm a.i. of STS; and (6) 6,600 ppm a.i. of STS. In this study, AVG was provided in a formulation as AVG-HCl at a concentration of 20%. STS was prepared using a 100 mM sodium thiosulfate treatment.

For each treatment, 23 palms were randomly selected covering about 15 hectares. The variety of plants used was a cross between Compact and Ghana. The plants were three years old at the time of treatment. A $CO_2$ sprayer was used to spray all treatments (100 mL/bunch) to bunches with 1 to 4 loose fruits. The time required to spray each bunch was about 8 seconds at 20 psi using a 2.0 full cone nozzle. The treatments were applied once per bunch. Ten and thirteen bunches per treatment were sprayed on Apr. 15 and 22, 2015, respectively.

Cumulative loose fruit (CLF) and cumulative loose mass (CLM) counts were determined on a daily basis for 14 days with the exception of day 4 and day 9 (for second spray only) and day 11 (after initial spray only) as measure to objectively quantify fruit abscission. An electronic balance was used to weigh all fruit. All loose fruit on the bunch, branches and on the ground was counted and weighed. The results are below in Table 1.

TABLE 1

| Treatment | Cumulative Loose Fruit | % Difference with UTC | Cumulative Loose Mass (g) | % Difference with UTC |
|---|---|---|---|---|
| UTC | 143.4 | — | 1101 | — |
| 500 ppm AVG | 72.0 | 71.4 | 321 | 70.8 |
| 240 ppm STS | 129.0 | 14.4 | 1106 | −0.4 |
| 720 ppm STS | 124.7 | 18.7 | 977 | 11.3 |
| 2,200 ppm STS | 159.1 | −15.7 | 1392 | −26.4 |
| 6,600 ppm STS | 117.5 | 25.9 | 1020 | 7.3 |

As seen in Table 1, STS did not consistently decrease cumulative loose fruit or cumulative loose mass. In this study, however, AVG performed very well providing 71.4 percent decrease in cumulative loose fruit and a 70.8 percent decrease in cumulative loose mass.

Applicant will initiate additional studies to determine if there is a better method for delivery of STS.

The invention claimed is:

1. A method of increasing oil content of oil palm fruit comprising applying a composition comprising an active ingredient consisting of an ethylene biosynthesis inhibitor selected from the group consisting of aminooxyacetic acid and rhyzobitoxin to oil palm fruit before the oil palm fruit is harvested, wherein from about 0.02 mg to about 20 g of the ethylene biosynthesis inhibitor per palm is applied per treatment from about three weeks before the fruit is harvested to about the day before the fruit is harvested.

2. The method of claim 1 wherein from about 0.02 mg to about 2 g of the ethylene biosynthesis inhibitor per palm is applied per treatment.

3. The method of claim 1 wherein the ethylene biosynthesis inhibitor is applied about every 7 to 21 days.

4. The method of claim 1 wherein the ethylene biosynthesis inhibitor is applied about every 10 to 14 days.

* * * * *